(12) United States Patent
Doerr et al.

(10) Patent No.: US 8,768,430 B2
(45) Date of Patent: Jul. 1, 2014

(54) MRT INTERFERENCE FIELD DETECTION MEDICAL IMPLANT WITH PRONE POSTURE POSITION SENSOR

(75) Inventors: Thomas Doerr, Berlin (DE); Ingo Weiss, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 775 days.

(21) Appl. No.: 12/972,466

(22) Filed: Dec. 18, 2010

(65) Prior Publication Data

US 2011/0148400 A1  Jun. 23, 2011

Related U.S. Application Data

(60) Provisional application No. 61/288,864, filed on Dec. 22, 2009.

(51) Int. Cl.
| | | |
|---|---|---|
| *A61B 5/103* | (2006.01) | |
| *A61N 1/37* | (2006.01) | |
| *A61B 5/00* | (2006.01) | |
| *A61B 5/11* | (2006.01) | |
| *A61B 5/06* | (2006.01) | |
| *G01R 33/28* | (2006.01) | |

(52) U.S. Cl.
CPC .............. *A61B 5/686* (2013.01); *A61B 5/6869* (2013.01); *A61B 5/7203* (2013.01); *A61B 5/1116* (2013.01); *A61N 1/37* (2013.01); *A61N 1/3718* (2013.01); *A61B 5/065* (2013.01); *G01R 33/285* (2013.01)

USPC ........... 600/410; 324/318; 324/322; 600/409; 600/411; 600/413; 600/415; 600/424; 600/425; 600/427; 600/428

(58) Field of Classification Search
USPC ................ 324/300–322, 207.11, 244, 251; 600/407–435, 436, 508, 529, 544; 382/128–133; 606/159; 378/205, 208; 5/600; 700/90
See application file for complete search history.

(56) References Cited

U.S. PATENT DOCUMENTS

| | | | |
|---|---|---|---|
| 6,937,883 B2 * | 8/2005 | Prince ........................... | 600/411 |
| 6,973,162 B2 * | 12/2005 | Block et al. .................... | 378/63 |
| 7,535,228 B2 * | 5/2009 | Tiernan et al. ............... | 324/318 |
| 7,672,712 B2 * | 3/2010 | Thomas et al. .............. | 600/436 |
| 7,701,209 B1 * | 4/2010 | Green .......................... | 324/307 |
| 7,725,157 B2 * | 5/2010 | Dumoulin et al. ........... | 600/410 |
| 7,835,785 B2 * | 11/2010 | Scully et al. ................. | 600/424 |
| 8,002,465 B2 * | 8/2011 | Ahn ............................. | 378/205 |
| 8,208,990 B2 * | 6/2012 | Maschke ...................... | 600/424 |
| 8,257,375 B2 * | 9/2012 | Maschke ...................... | 606/159 |

(Continued)

FOREIGN PATENT DOCUMENTS

| | | | |
|---|---|---|---|
| EP | | 1731088 A1 | 12/2006 |
| WO | WO 2008026970 A1 | | 3/2008 |

OTHER PUBLICATIONS

European Search Report dated Apr. 21, 2011 (8 pages).

*Primary Examiner* — Melissa Koval
*Assistant Examiner* — Tiffany Fetzner
(74) *Attorney, Agent, or Firm* — ARC IP Law, PC; Joseph J. Mayo

(57) ABSTRACT

Allows the specificity of an automatic MRT detection to be increased in a simple manner. This is achieved using an automatically calibrating position sensor, so that the user does not have to perform additional calibration of this sensor. Incorrect sensor calibrations are thus eliminated as well.

19 Claims, 3 Drawing Sheets

(56) References Cited

U.S. PATENT DOCUMENTS

| | | |
|---|---|---|
| 2003/0083588 A1* | 5/2003 | McClure et al. ............. 600/547 |
| 2003/0195413 A1* | 10/2003 | Rubin et al. ................. 600/411 |
| 2005/0080461 A1 | 4/2005 | Stahmann et al. |
| 2005/0272995 A1* | 12/2005 | Prince .......................... 600/407 |
| 2007/0039101 A1* | 2/2007 | Luginbuhl et al. ................. 5/600 |
| 2007/0078334 A1* | 4/2007 | Scully et al. ................. 600/424 |
| 2007/0222433 A1* | 9/2007 | Tiernan et al. ........... 324/207.21 |
| 2008/0009700 A1* | 1/2008 | Dumoulin et al. ............ 600/410 |
| 2008/0154342 A1 | 6/2008 | Digby et al. |
| 2009/0129556 A1* | 5/2009 | Ahn .............................. 378/208 |
| 2009/0187096 A1* | 7/2009 | Tiernan et al. ................ 600/421 |
| 2010/0241147 A1* | 9/2010 | Maschke ...................... 606/159 |
| 2011/0046474 A1* | 2/2011 | Roessler ....................... 600/413 |
| 2011/0082366 A1* | 4/2011 | Scully et al. ................. 600/424 |
| 2011/0148400 A1* | 6/2011 | Doerr et al. ............. 324/207.11 |

\* cited by examiner

MRT INTERFERENCE FIELD DETECTION MEDICAL IMPLANT WITH PRONE POSTURE POSITION SENSOR

This application claims the benefit of U.S. Provisional Patent Application 61/288,864, filed on Dec. 22, 2009, which is hereby incorporated by reference in its entirety.

BACKGROUND OF THE INVENTION

1. Field of the Invention

Embodiments of the invention relate a device and a method for detecting electromagnetic fields which occur in tests using magnetic resonance tomography imaging devices. ("MRT" or "MRI" stand for magnetic resonance tomography and magnetic resonance imaging respectively, wherein these two acronyms are used interchangeably herein).

2. Description of the Related Art

Although MRI testing is becoming increasingly important in diagnostic medicine, it is contraindicated for some patients. Such contraindication may result from an at least partially implanted medical device (also referred to below as "implant" or "IMD").

In order to still allow MRI testing, various approaches are known which relate either to performing the MRI testing or to the implantable medical device.

Although the prior art provides methods for detecting MRI fields, these methods are frequently based on single measuring methods.

US 2008/0154342 describes a method which uses a giant magnetoresistance (GMR) sensor to detect problematic magnetic fields from MRT devices. Thus, this method relies on a single parameter, the measured field intensity.

BRIEF SUMMARY OF THE INVENTION

The object of one or more embodiments of the invention is to provide a device and a method for medical devices and implantable medical devices which eliminate the disadvantages of the prior art and allow the detection of MRI fields to be verified. The object is achieved by use of an implantable medical device (IMD) having the features as claimed herein.

The IMD contains at least one unit for detecting MRI interference fields, the unit having at least one sensor and/or indicator for electromagnetic interference fields or magnetic fields typical for MRI, at least one control unit which may be connected to the unit for detecting electromagnetic interference fields or magnetic fields, containing at least one diagnostic unit and/or at least one treatment unit, wherein the unit for detecting MRI interference fields also has a position sensor, and the unit for detecting MRI interference fields detects interference from MRI interference fields only when, in addition to at least one sensor and/or at least one indicator for electromagnetic interference fields or magnetic fields typical for MRI, the position sensor indicates a prone posture of the patient.

The term "prone posture" is understood to mean a horizontal position of the patient. The term "indicators for MRI interference fields" refers to measurements which indicate electromagnetic interference fields.

"MRI interference fields" refers to electromagnetic fields produced in the surroundings of an MRI device by the MRI device. Examples of "interference fields typical for MRI" include, but are not limited to, a static magnetic field, a gradient field, and an electromagnetic radio frequency (RF) field. The diagnostic unit may be, for example, but is not limited to, a unit for determining physical and/or chemical and/or biological parameters, and the treatment unit may be, for example, but is not limited to, a unit for delivering electrical pulses and/or chemical substances and/or mechanical forces.

However, if the specificity of the MRT detection is limited, there is considerable risk that the implant will be switched, also outside the MRT surroundings, to an MRT mode by other environmental influences, likewise resulting in endangerment of the patient.

In a prone position (during sleep), however, many of the environmental conditions which may be confused with MRT are excluded, so that the additional evaluation of the position information greatly increases specificity for the MRT detection.

It is preferred that the position sensor is self-calibrating, whereby a prone posture is automatically detected, and/or the calibration is triggered via an external device, such as a patient device and/or programming device, and/or the prone posture is verified via an external device, such as a patient device and/or programming device.

It is particularly preferred that the calibration of the position sensor, preferably calibration during night sleep, is carried out after evaluation of the time of day.

It is further preferred that for identification of a prone posture the diurnal phases with minimum heart rate are evaluated. In this manner, for example, night sleep which is preferably used for a calibration may be identified.

It is also preferred that night sleep is identified by the evaluation of the heart rate variability and the circadian rhythm thereof.

It is also preferred that night sleep is identified by evaluating the respiratory rate.

It is also preferred that night sleep is identified by evaluating the patient activity.

It is also preferred that night sleep is identified by evaluating at least one EEG parameter. EEG is also known as electroencephalography.

It is further preferred that detection of MRI interference fields initiates a predeterminable reaction of the IMD only within a predeterminable time window.

It is also preferred that the unit for detecting MRI interference fields includes at least one of the following sensors and/or indicators: a GMR sensor, a MagFET sensor, a Hall sensor, an electro-optical converter as indicator, monitoring of battery voltages during capacitor charging processes as indicator, detection of RF fields as indicator, detection of magnetic gradient fields as indicator, and detection of currents induced by electromagnetic fields as indicator.

It is also preferred that at least one of the following measures is initiated with the identification of electromagnetic interference fields by the unit for detecting MRI interference fields: changing to an MRI-safe state, remaining for a prolonged period of time in an MRI-safe state or a state that is insensitive to electromagnetic interference fields, emission of electromagnetic pulses for signaling that an IMD is present in the electromagnetic field, for signaling to an MRI device, with the possibility of thus transmitting information as well as the interference and displaying same on the screen of the MRI device, and allowing the administration of treatment and/or the detection of electrical states of the tissue only in time windows in which no electromagnetic interference fields are detected and/or a reconstruction of a measurement is carried out for the regions in which the detection is not allowed on account of detected electromagnetic interference fields.

The object is further achieved by use of a method for increasing the specificity in the detection of MRI interference fields as claimed herein, wherein for detection of an MRI interference field, in addition to the detection by at least one sensor and/or at least one indicator for electromagnetic interference fields typical for MRI, the prone posture of the implant carrier is also detected. The method may be carried out, for example, using an IMD as described above.

BRIEF DESCRIPTION OF THE DRAWINGS

Several aspects of the invention are illustrated in FIGS. 1 through 3.

DETAILED DESCRIPTION OF THE INVENTION

Figure 1:
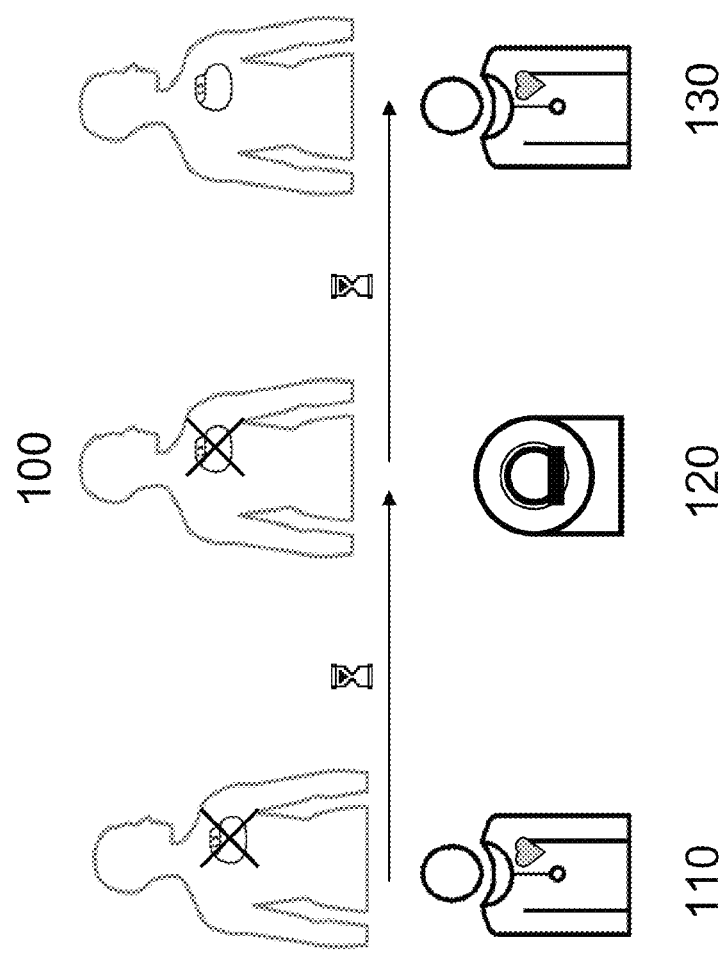
FIG. 1 shows a schematic illustration of the sequence of an MRI test.

FIG. 1 illustrates the starting situation, using an ICD (implantable defibrillator/cardioverter) as an example. The ICD patient 100 receives follow-up care from a cardiologist before the planned MRT test, and the ICD is switched off 110. After a time delay of hours to days the MRT test is performed by a radiologist 120. After a further delay the patient is once again under the care of the cardiologist 130, and the ICD is switched back on. During the entire time from 110 to 130 the patient is without the protection of the implanted defibrillator, and is essentially without rhythm monitoring. This residual risk is currently accepted in return for the benefits of the MRT test. In addition, the economic and logistic expenditure for such a procedure is very high, and in many cases rules out emergency use of MRT.

Figure 2:
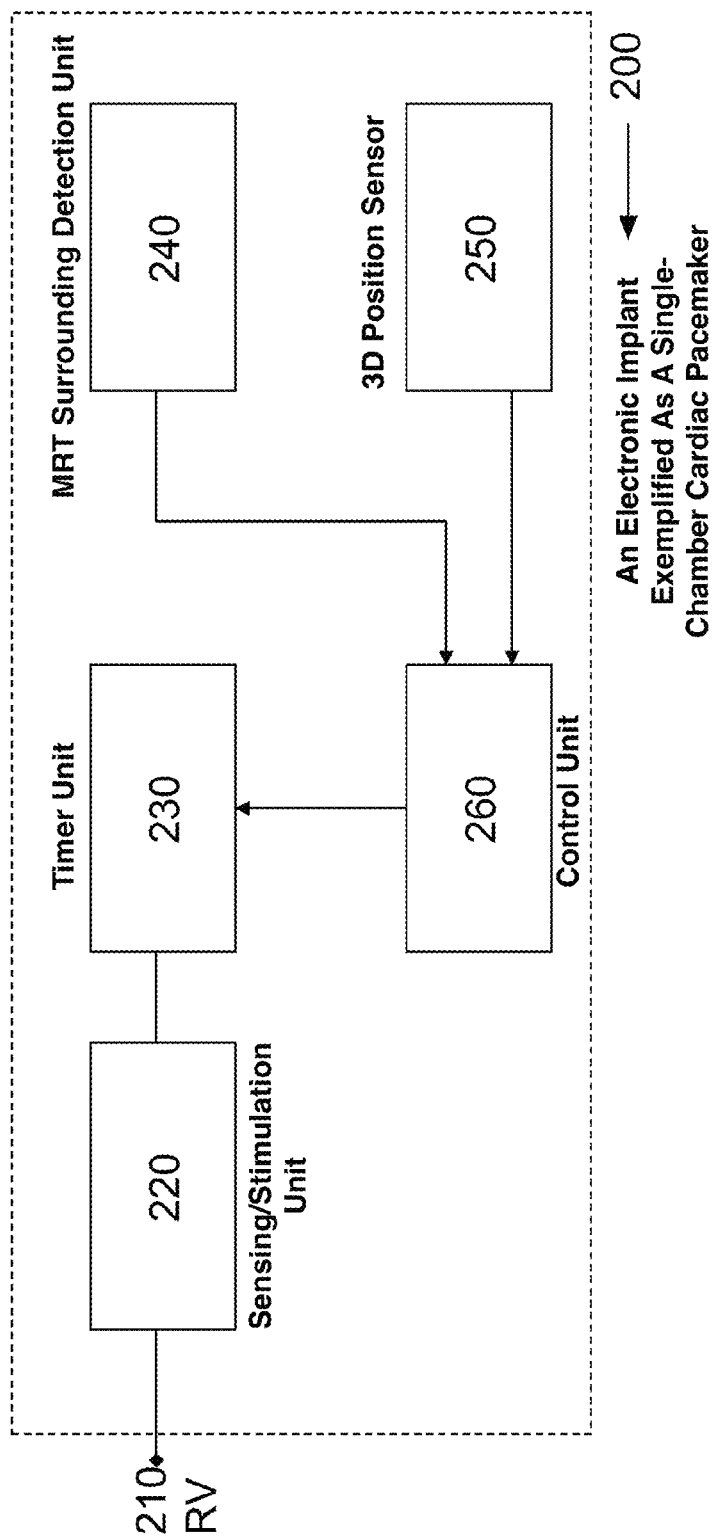
FIG. 2 shows a simplified block diagram of an IMD according to the invention.

FIG. 2 shows a simplified block diagram of an electronic implant 200, for example a single-chamber cardiac pacemaker. This implant has a sensing and stimulation unit 220, connected to the right ventricular electrode terminal 210, and a timer unit 230 for demand-controlled stimulation of the heart.

The electronic implant also contains at least one unit for detecting MRT surroundings 240, such as but not limited to a giant magnetoresistance (GMR) sensor 240.

According to the invention, this block diagram is supplemented by a three-dimensional position sensor 250. The two sensor signals are evaluated in a specialized control unit, and when the MRT sensor 240 indicates MRT surroundings and the position sensor 250 signals a prone position of the patient, the control unit 260 switches the timer unit 230 to a preprogrammed MRT-safe operating mode, for example but not limited to V00 or D00 for patients dependent on a pacemaker.

Figure 3:
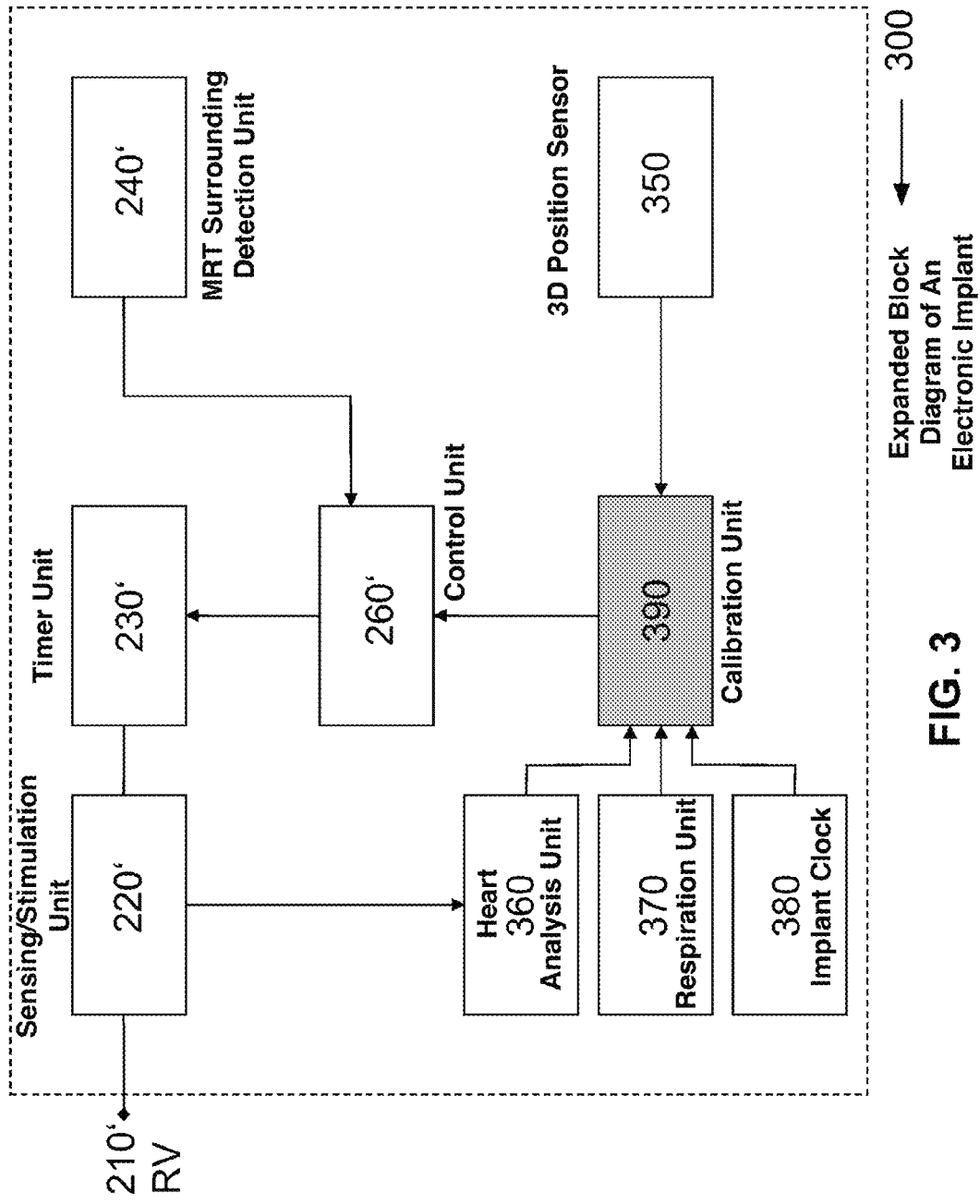
FIG. 3 shows a variant of a simplified block diagram of an electronic implant according to the invention.

FIG. 3 illustrates an expanded block diagram of electronic implant 300. In this case an additional calibration unit 390 is introduced. This calibration unit is used to automatically determine the prone position of the patient. For this purpose the calibration unit is connected to the three-dimensional position sensor 350, a unit 360 for analyzing the cardiac rhythm, a unit 370 for determining the respiratory rate, and the implant clock 380. Element 210' is the right ventricular electrode terminal, 220' is the sensing and stimulation unit, 230' is the timer unit, 240' is the unit for detecting MRT surroundings and 260' is the control unit. See also FIG. 2 for further description of these elements.

The calibration unit 390 stores and updates reference data of the position sensor 350 whenever the parameters from the heart rate analysis unit 360 (minimum heart rate, heart rate variability), the respiratory rate analysis unit 370, and the implant time 380 (comparison with day/night switchover parameters) suggest night sleep.

The calibration unit 390 continuously compares this current reference value to the current value of the position sensor 350, and signals a prone position of the control unit 260' whenever the current value and reference value match.

Embodiments of the invention allow the specificity of an automatic MRT detection to be increased in a simple manner. This is achieved using an automatically calibrating position sensor, so that the user does not have to perform additional calibration of this sensor. Incorrect sensor calibrations are thus eliminated as well.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implantable medical device comprising a cardiac pacemaker that also comprises:
    a magnetic resonance imaging interference fields detection unit, comprising
        at least one sensor, or at least one indicator, or both configured to detect electromagnetic interference fields typcial of magnetic resonance imaging or magnetic fields typical of magnetic resonance imaging;
    at least one control unit coupled to the magnetic resonance imaging interference fields detection unit comprising
        at least one diagnostic unit or
        at least one treatment unit,
        or both said at least one diagnostic unit and said at least one treatment unit;
    a position sensor coupled to the at least one control unit;
    wherein the magnetic resonance imaging interference fields detection unit is configured to detect interference from magnetic resonance imaging interference fields only when, in addition to the at least one sensor, or the at least one indicator, or both the at least one sensor and the at least one indicator that are configured to detect electromagnetic interference fields typcial of magnetic resonance imaging, the position sensor indicates a prone posture of a patient associated with said implantable medical device;
    a calibration unit coupled to said position sensor and configured to automatically detect the prone posture from said position sensor;
    wherein the calibration unit is connected to said position sensor and to one or more of
        a heart analysis detection unit,
        a respiratory rate detection unit, and
        an implant clock;
    wherein the calibration unit is further configured to detect one or more parameter values from one or more of said heart analysis detection unit, said respiratory rate detection unit and said implant clock; and,
    wherein the calibration unit is further configured to store and update data from said position sensor when said one or more detected parameter values suggest night sleep.

2. The implantable medical device according to claim 1, wherein the position sensor is self-calibrating.

3. The implantable medical device according to claim 2, wherein the calibration of the position sensor is carried out after evaluation of a time of day from said implant clock.

4. The implantable medical device according to claim 1, wherein the identification of the prone posture include evaluation of diurnal phases with minimum heart rate that are evaluated from said heart analysis detection unit.

5. The implantable medical device according to claim 1, wherein the at least one control unit is configured to identify night sleep by an evaluation of a heart rate variability and a circadian rhythm thereof from said heart analysis detection unit.

6. The implantable medical device according to claim 1, wherein the at least one control unit is configured to identify night sleep by an evaluation of a respiratory rate from said respiratory rate detection unit.

7. The implantable medical device according to claim 1, wherein the at least one control unit is configured to identify night sleep by an evaluation of patient activity.

8. The implantable medical device according to claim 1, wherein the at least one control unit is configured to identify night sleep by an evaluation at least one EEG parameter.

9. The implantable medical device according to claim 1, wherein detection of magnetic resonance imaging interference fields initiates a predeterminable reaction of the implantable medical device only within a predeterminable time window.

10. The implantable medical device according to claim 1, wherein the unit configured to detect magnetic resonance imaging interference fields includes at least one of the following sensors and/or indicators:
  a GMR sensor,
  a MagFET sensor,
  a Hall sensor,
  an electro-optical converter,
  a battery voltage sensor configured to monitor voltage during capacitor charging,
  an RF field detector,
  a magnetic gradient field detector,
  a current detector configured to detect currents induced by electromagnetic fields.

11. The implantable medical device according to claim 1, wherein upon identification of electromagnetic interference fields by the unit configured to detect magnetic resonance imaging interference fields, the at least one control unit is configured to:
  change to magnetic resonance imaging-safe state,
  remain for a prolonged period of time in the magnetic resonance imaging-safe state or a state that is insensitive to electromagnetic interference fields,
  emit electromagnetic pulses in order to signal that the implantable medical device is present in an electromagnetic field,
  transmit information including an interference,
  display said interference on a screen of a magnetic resonance imaging device, and
  allow administration of treatment and/or detection of electrical states of tissue only in time windows in which no electromagnetic interference fields are detected and/or carry out a reconstruction of a measurement in regions in which the detection is not allowed on account of detected electromagnetic interference fields.

12. The implantable medical device according to claim 1, wherein said calibration unit is further configured to continuously compare said one or more detected parameter values to said detected prone posture.

13. The implantable medical device according to claim 12, wherein said calibration unit is further configured to send a prone position signal to said at least one control unit when said one or more detected parameter values match said detected prone posture.

14. The implantable medical device according to claim 1, further comprising a timer unit, wherein when said magnetic resonance imaging interference fields detection unit detects interference from magnetic resonance imaging interference fields and when said position sensor indicates a prone posture, said at least one control unit is further configured to switch said timer unit to a preprogrammed MRT-safe operating mode.

15. The implantable medical device according to claim 1, wherein the magnetic resonance imaging interference fields detection unit is located within said implantable medical device.

16. The implantable medical device according to claim 1, wherein the position sensor is located within said implantable medical device.

17. A method comprising:
  increasing the specificity in the detection of magnetic resonance imaging interference fields using an implantable medical device comprising:
    a magnetic resonance imaging interference fields detection unit, comprising
      at least one sensor, or at least one indicator, or both configured to detect electromagnetic interference fields typcial of magnetic resonance imaging or magnetic fields typcial of magnetic resonance imaging;
    at least one control unit coupled to the magnetic resonance imaging interference fields detection unit, comprising
      at least one diagnostic unit or
      at least one treatment unit,
      or both said at least one diagnostic unit and said at least one treatment unit;
    a position sensor coupled to the at least one control unit;
    wherein the magnetic resonance imaging interference fields detection unit is configured to detect magnetic resonance imaging interference fields only when, in addition to the at least one sensor or the at least one indicator or both the at least one sensor and the at least one indicator that are configured to detect electromagnetic interference fields typcial of magnetic resonance imaging, the position sensor indicates a prone posture of a patient associated with said implantable medical device;
    a calibration unit coupled to said position sensor and configured to automatically detect the prone posture from said position sensor;
    wherein the calibration unit is connected to said position sensor and to one or more of
      a heart analysis detection unit,
      a respiratory rate detection unit, and
      an implant clock;
    wherein the calibration unit is further configured to detect one or more parameter values from one or more of said heart analysis detection unit, said respiratory rate detection unit and said implant clock;
    wherein the calibration unit is further configured to store and update data from said position sensor when said one or more detected parameter values suggest night sleep.

18. The method according to claim 17, further comprising placing the magnetic resonance imaging interference fields detection unit within said implantable medical device.

19. The method according to claim 17, further comprising placing the position sensor within said implantable medical device.

* * * * *